United States Patent [19]

Böger et al.

[11] Patent Number: 4,731,090
[45] Date of Patent: Mar. 15, 1988

[54] PROCESS FOR PROTECTING KERATINOUS MATERIAL FROM ATTACK BY INSECTS FEED ON KERATIN WITH PYRIDYLOXYTRIFLUOROMETHANESULFONANILIDES

[75] Inventors: Manfred Böger, Weil am Rhein, Fed. Rep. of Germany; Bernardo de Sous, Riehen, Switzerland; Dieter Reinehr, Kandern, Fed. Rep. of Germany; Werner Schmid, Riehen; Hermann Rempfler, Ettingen; Hans Tobler, Allschwil, all of Switzerland

[73] Assignee: Ciba-Geigy Corporation, Ardsley, N.Y.

[21] Appl. No.: 680,685

[22] Filed: Dec. 12, 1984

[30] Foreign Application Priority Data

Dec. 23, 1983 [CH] Switzerland ............... 6885/83

[51] Int. Cl.⁴ .................. D06M 3/00; C07D 213/64
[52] U.S. Cl. .................. 8/127.5; 8/128 R; 546/293; 546/287; 546/288
[58] Field of Search .................. 546/293, 287, 288; 514/344, 347; 8/127.5, 128 R

[56] References Cited

U.S. PATENT DOCUMENTS

| | | | |
|---|---|---|---|
| 3,066,166 | 11/1962 | Muth et al. | 564/97 |
| 3,686,192 | 8/1972 | Moore et al. | 546/293 |
| 4,348,221 | 9/1982 | Szczepanski et al. | 546/302 |
| 4,425,156 | 1/1984 | Pissiotas et al. | 546/288 |
| 4,562,213 | 12/1985 | Nishida et al. | 546/301 |

FOREIGN PATENT DOCUMENTS 890883 9/1953 Fed. Rep. of Germany.
1058049 9/1969 Fed. Rep. of Germany.

Primary Examiner—Henry R. Jiles
Assistant Examiner—Dale A. Bjorkman
Attorney, Agent, or Firm—Edward McC. Roberts

[57] ABSTRACT

A process for protecting keratinous material with the aid of substantially novel pyridyloxytrifluoromethanesulfonanilides from pests that feed on keratin, said pyridyloxytrifluoromethanesulfonanilides having the formula

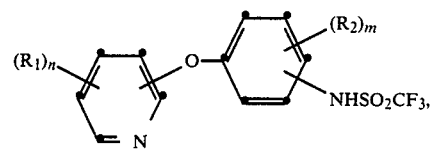

wherein $R_1$ and $R_2$, each independently of the other, are halogen, haloalkyl, alkyl, nitro, cyano, alkoxy or haloalkoxy or alkoxycarbonyl, and n and m, each independently of the other, are 0 or a value from 1 to 3, with the proviso that if n or m > 1, the substituents $R_1$ and $R_2$ may be identical or different, and that at least one substituent selected from the group consisting of halogen, haloalkyl and haloalkoxy is present in the molecule.

The preparation of these compounds and the use thereof as active ingredients of compositions providing a mothproof and beetle-resistant finish are also described herein.

11 Claims, No Drawings

PROCESS FOR PROTECTING KERATINOUS MATERIAL FROM ATTACK BY INSECTS FEED ON KERATIN WITH PYRIDYLOXYTRIFLUOROMETHANESULFONANILIDES

The present invention relates to a process for providing keratinous material with a protective finish against attack by insects that feed on keratin, which process comprises treating said keratinous material with specific pyridyloxytrifluoromethanesulfonanilides. The invention further relates to novel pyridyloxytrifluoromethanesulfonanilides, to the preparation thereof, to compositions containing said compounds and to the use thereof for providing keratinous material with a mothproof and beetle-resistant protective finish.

Chloromethanesulfonamides of polynuclear amines, including halogenated phenoxychloromethanesulfonanilides, which can be employed as protectants against textile pests as well as against attack by mould and bacteria are known from DE-A 890 883, DE-A 1 058 049 and U.S. Pat. No. 3,066,166.

Surprisingly, it has now been found that specific pyridyloxytrifluoromethanesulfonanilides are most suitable for use as protectants against insects that feed on keratin. Some of these pyridyloxytrifluoromethanesulfonanilides are known from U.S. Pat. No. 3,686,192 where they are described as active herbicides and anti-inflammatory agents.

The process of this invention for providing keratinous material with a protective finish against attack by insects that feed on keratin comprises treating the material to be protected with compounds of the formula

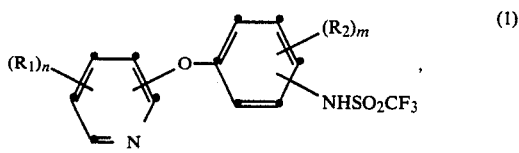

(1)

wherein $R_1$ and $R_2$, each independently of the other, are halogen, haloalkyl, alkyl, nitro, cyano, alkoxy, haloalkoxy or alkoxycarbonyl, and n and m, each independently of the other, are 0 or value from 1 to 3, with the proviso that if n or m > 1, the substituents $R_1$ and $R_2$ may be identical or different, and that at least one substituent selected from the group consisting of halogen, haloalkyl and haloalkoxy is present in the molecule, or salts thereof.

Furthermore, the invention relates to the use of compounds of formula (1) as protectants for keratinous material against insects that feed on keratin as well as to material which has been provided with a protective finish with the aid of a compound of formula (1).

In formula (1) halogen will be understood as comprising all halogen atoms, in particular chlorine, bromine and fluorine, with chlorine being preferred. Unsubstituted and substituted alkyl and alkoxy groups contain in particular 1 to 6 carbon atoms, preferably 1 to 4 carbon atoms. Haloalkyl and haloalkoxy groups contain preferably chlorine and/or fluorine as halogen atoms. Alkoxycarbonyl groups contain 2 to 5 carbon atoms, preferably 2 carbon atoms.

The compounds contain in the molecule, in addition to the —$NHSO_2CF_3$ group, at least one halogen or halogen-containing substituent. In preferred compounds the total number of the substituents $R_1$ and $R_2$ is 1 to 4 (n+m=1 to 4), preferably 2 to 4 (n+m=2 to 4). If several substituents ($R_1$ or $R_2$) are present in the pyridine or phenyl nucleus, these may of course be identical or different. The compounds of formula (1) contain preferably not more than 3, in particular not more than 2, and most preferably not more than 1, of the substituents haloalkyl, nitro, cyano and haloalkoxy. These substituents occur preferably as $R_1$.

The compounds of formula (1) can also be used in the process of this invention in the form of their salts. Among the salts, particular mention is to be made of the alkali metal salts and ammonium salts (including substituted ammonium salts which are derived from amines). Preferred salts are e.g. sodium, potassium and ammonium salts.

In the process of this invention it is advantageous to use such compounds of formula (1) wherein the sum of n+m is at least 2 if $R_1$ or $R_2$ is halogen.

In particular such compounds of formula (1) are used wherein each of $R_1$ and $R_2$ independently of the other is chlorine, fluorine, $C_1$–$C_4$-haloalkyl, wherein halogen is chlorine and/or fluorine, or is $C_1$–$C_4$-alkyl, $C_1$–$C_4$alkoxy, $C_1$–$C_4$alkoxycarbonyl, nitro or cyano, especially such compounds wherein at least one of the substituents $R_1$ or $R_2$, preferably $R_1$, is chlorine or $C_1$–$C_4$haloalkyl, preferably trifluoromethyl, with preferably one of the substituents $R_1$ being haloalkyl, in particular trifluoromethyl.

In preferred compounds of formula (1) the sum of n+m is 1 to 4, in Particular 2 to 4. Further preferred compounds of formula (1) are those in which the $NHSO_2CF_3$ group is in the 4-position, and of such compounds particular mention is to be made of those which carry $C_1$–$C_4$alkyl, preferably methyl, in one or both ortho-positions relative to the —$NHSO_2CF_3$ group.

Further, in the process of this invention it is particularly advantageous to use those compounds of formula (1) wherein the pyridine ring is attached in the 2-position to the oxygen atom.

Compounds of particular interest of formula (1) which can be used in the process of this invention have the formula

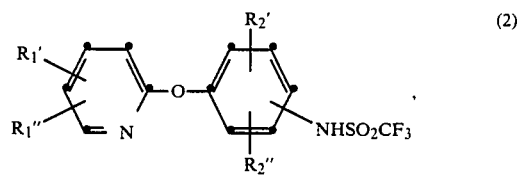

(2)

wherein $R'_1$ is chlorine or $C_1$–$C_4$haloalkyl, wherein halogen is chlorine and/or fluorine, preferably trifluoromethyl, $R''_1$ is hydrogen, chlorine or $C_1$–$C_4$alkyl, $R'_2$ is hydrogen, $C_1$–$C_4$alkoxycarbonyl, $C_1$–$C_4$alkyl or chlorine and $R''_2$ is hydrogen, $C_1$–$C_4$alkyl or chlorine, with particularly good results being obtained from compounds of the formula

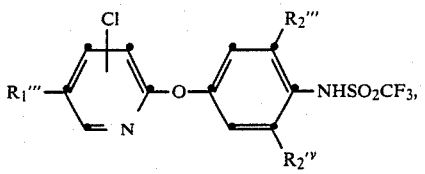

wherein R"₁' is trifluoromethyl or chlorine and each of R"₂' and R₂'ᵛ independently of the other is hydrogen, $C_1$–$C_4$alkyl or —COOCH₃.

The compounds of formula (1) which can be used in the process of the invention for protecting keratinous material against insects that feed on keratin are effective in particular for example against Lepidoptera larvae such as Tineola spec. and Tiena spec., and also Coleoptera larvae, e.g. Anthrenus sepc. and Attagenus spec. The compounds are most suitable for proofing keratinous material against feeding damage by insects, especially for providing such material with a washfast and lightfast protective finish against insects, in particular moths and beetles. The keratinous material to be proofed can be both in the raw and in the processed state, for example raw or processed sheep's wool or products made of other animal hairs, hides, furs and feathers.

A particularly important feature is the effectiveness of the compounds of formula (1) against the larvae of the webbing clothes moth (*Tineola bisselliella*), the common clothes moth (*Tiena pellionella*) and of the false clothes moth (*Hofmannophila pseudopretella*), as well as against the larvae of fur beetles and carpet beetles (Attagenus spec. and Anthrenus spec. respectively), e.g. against larvae of *Anthrenus verbasci* and *Anthrenus pimpinellae*, of *Anthrenus scrophulariae*, of *Anthrenus fasciatus*, *Attagenus pellio* and, in particular, of the black fur beetle (*Attagenus piceus*) and of the carpet bug (*Anthrenus flavipes*).

The process of the present invention is therefore preferably used on the one hand for protecting woollen textiles, for example blankets, wool carpets, woollen underwear, woollen clothing, knits and wool-containing textiles such as blends, one component of which is wool, for example blends of wool and other natural fibres, preferably cotton, or of wool and synthetic fibres, and, on the other hand, also for protecting furs and skins from attack by the abovementioned pests.

The compounds of formula (1) are applied to the above substrates, in particular to woollen textiles and wool-containing textiles, preferably by processes commonly known and employed in dyeing, such as the exhaust process and padding. To this end, an aqueous solution or dispersion (or emulsion or suspension) of the respective active substance is formulated. The active substance can be dissolved beforehand in an organic solvent, such as an aliphatic or alicyclic alcohol, a ketone, a hydrocarbon, such as benzene, a xylene, toluene, a petroleum distillate, and also a chlorinated or fluorinated hydrocarbon, especially in propylene glycol, methoxy ethanol, ethoxy ethanol or dimethylformamide, and then added to the treatment bath, which can contain additional assistants conventionally used in dyeing, for example dispersants, wetting agents, acids, bases and/or dyes. The organic stock formulation can already contain such assistants.

The textile materials can be impregnated e.g. with hot or cold aqueous dye, bleaching, chroming or aftertreatment baths containing the active ingredients. Various textile finishing processes are possible, for example the pad or exhaust process.

The treatment is conveniently carried out in the temperature range from 10° to 100° C., in the dye bath preferably in the range from about 60° to 100° C. and in the aftertreatment or wash bath preferably in the range from 10° to 70° C., preferably from 20° to 60° C.

As further assistants there may be added to the treatment baths e.g. dispersants, emulsifiers or surfactants. The liquor can additionally contain further conventional assistants, such as water-soluble perborates, polyphosphates, carbonates, silicates, fluorescent whitening agents, softeners, salts with acid reaction, such as ammonium or zinc silicofluoride, or certain organic acids such as oxalic acid, acetic acid or, in particular, formic acid, and also antimicrobial agents and finishing agents, for example those based on synthetic resins or starch. If the mothproof and beetle-resistant finishing is carried out together with the dyeing of the material (e.g. wool), the baths additionally contain the corresponding dyes and, if appropriate, the necessary assistants, e.g. levelling agents.

The aqueous treatment baths contain, for example, surfactants, for example anionic compounds, such as soaps and other carboxylates (e.g. alkali metal salts of higher fatty acids), derivatives of sulfur oxyacids (e.g. the sodium salt of dodecylbenzenesulfonic acid, water-soluble salts of sulfuric acid monoesters of higher molecular alcohols or of their polyglycol ethers, for example soluble salts of dodecyl alcohol sulfate or of dodecyl alcohol polyglycol ether sulfate), derivatives of phosphorus oxyacids (e.g. phosphates), derivatives with acid (electrophilic) nitrogen in the hydrophilic group (e.g. disulfine salts), cationic surface-active agents, such as amines and their salts (e.g. lauryldiethylenetriamine), onium compounds, amine oxides or nonionic surface-active agents, such as polyhydroxy compounds, surface-active agents based on mono- or polysaccharides, higher molecular acetylene glycols, polyglycol ethers (e.g. polyglycol ethers of higher fatty alcohols, polyglycol ethers of higher molecular alkylated phenols).

If non-aqueous application is made (solvent application), an appropriate amount of a compound of formula (1) may also be added to a suitable solvent and the material to be protected may be impregnated with the solution so obtained. Suitable solvents for this application are, inter alia, trichloroethylene, methylene chloride, hydrocarbons, propylene glycol, methoxyethanol, ethoxyethanol, dimethylformamide, to which dispersants (e.g. emulsifiers, such as sulfated castor oil, fatty alcohol sulfates etc) and/or other assistants can be added. The material to be protected is usually simply impregnated with these solutions.

The proofing of the material to be protected may also be combined with a dry cleaning process. To this end, an appropriate amount of a compound of formula (1) is dissolved in the cleansing agent (such as a lower halogenated alkane, e.g. trichloroethylene etc.) and the cleaning process is carried out in the usual manner.

However, an amount of a compound of formula (1) may also be dissolved in a readily volatile organic solvent and the resulting solution then sprayed onto the substrate to be protected (spray application).

Textile fabrics which contain wool, furs and feathers are particularly suitable for this application. The advantage of the spray application is that pollution of the wastewaters is avoided on account of the recovery of the solvent.

In the process of the present invention, the compounds of formula (1) may also be used in combination with other protectants which act against insects that feed on keratin, for example with urea derivatives, benzimidazoles, aromatic sulfonamides and phosphoric and phosphonic acid esters, synthetic pyrethroids and 5-phenylcarbamoylbarbituric acid derivatives.

The amount of compound of formula (1) which is added to the treatment bath or non-aqueous solvent depends on the substrate and the method of application. However, this amount is ordinarily such that, after application to the material which it is desired to protect, the latter contains about 10 to 2000 ppm, preferably 100 to 1000 ppm, of compound of formula (1) with the upper limit being largely determined by economic considerations, whereas the lower limit depends on criteria such as the intended breadth and permanency of the protective action. This corresponds, for example, to concentrations of 0.001 to 1 g of active ingredient per liter of treatment bath using the exhaust process at a liquor to goods ratio of 1:20, depending on the degree of exhaustion attainable. In the pad process concentrations of up to 2 g of active ingredient per liter are possible.

The invention also relates in particular to novel pyridyloxytrifluoromethanesulfonanilides of the formula

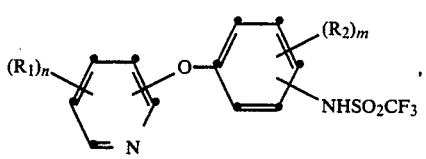
(1a)

wherein $R_1$ and $R_2$, each independently of the other, are halogen, haloalkyl, alkyl, nitro, cyano, alkoxy, haloalkoxy or alkoxycarbonyl, and n and m, each independently of the other, are 0 or a value from 1 to 3, with the proviso that if n or m > 1, the substituents $R_1$ and $R_2$ may be identical or different, and that at least one substituent selected from the group consisting of halogen, haloalkyl and haloalkoxy is present in the molecule, and the sum of n+m is at least 2 if $R_1$ or $R_2$ is halogen, and salts thereof.

The further explanations following formula (1) apply to the individual substituents and the salts of the novel compounds.

The compounds of formula (1a) contain in the molecule, in addition to the —$NHSO_2CF_3$ group, at least one halogen or halogen-containing substituent. In preferred compounds the total number of the substituents $R_1$ and $R_2$ is 1 to 4 (n+m=1 to 4), preferably 2 to 4 (n+m=2 to 4). If several substituents ($R_1$ or $R_2$) are present in the pyridine or phenyl nucleus, these may of course be identical or different. The compounds of formula (1a) contain preferably not more than 3, in particular not more than 2, and most preferably not more than 1, of the substituents haloalkyl, nitro, cyano, haloalkoxy and alkoxycarbonyl. These substituents occur preferably as $R_1$.

Particular mention is to be made of such compounds of formula (1a) wherein each of $R_1$ and $R_2$ independently of the other is chlorine, fluorine, $C_1$-$C_4$haloalkyl, wherein halogen is chlorine and/or fluorine, or is $C_1$-$C_4$alkyl, $C_1$-$C_4$alkoxy, nitro or cyano, especially such compounds wherein at least one of the substituents $R_1$ or $R_2$, preferably $R_1$, is chlorine or $C_1$-$C_4$haloalkyl, preferably trifluoromethyl, with preferably one of the substituents $R_1$ being $C_1$-$C_4$haloalkyl, in particular trifluoromethyl.

In preferred compounds of formula (1a) the sum of n+m is 1 to 4, in particular 2 to 4. Further preferred compounds of formula (1a) are those in which the $NHSO_2CF_3$ group is in the 4-position, and of such compounds particular mention is to be made of those which carry $C_1$-$C_4$alkyl, preferably methyl, in one or both ortho-positions relative to the —$NHSO_2CF_3$ group.

Those compounds of formula (1a) wherein the pyridine ring is attached in the 2-position to the oxygen atom have proved to be particularly advantageous.

Compounds of particular interest are pyridyloxytrifluoromethanesulfonanilides of the formula

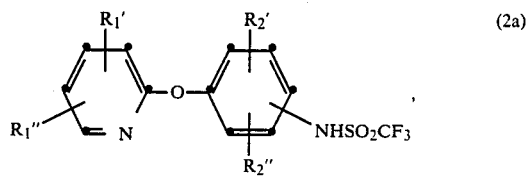
(2a)

wherein $R'_1$ is chlorine or $C_1$-$C_4$haloalkyl, wherein halogen is chlorine or fluorine, $R''_1$ is hydrogen, chlorine or $C_1$-$C_4$alkyl, $R'_2$ is hydrogen, $C_1$-$C_4$alkoxycarbonyl, $C_1$-$C_4$alkyl or chlorine and $R''_2$ is hydrogen, $C_1$-$C_4$alkyl or chlorine, with the provisos stated under formula (1a) with regard to the meanings of the substituents applying: compounds of the formula

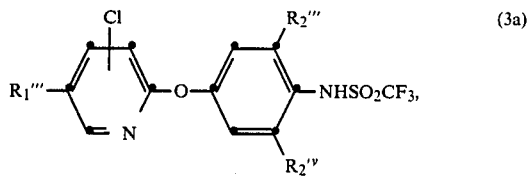
(3a)

wherein $R'''_1$ is trifluoromethyl or chlorine and each of $R'''_2$ and $R_2'^{iv}$ independently of the other is hydrogen or $C_1$-$C_4$alkyl, are particularly effective against pests that feed on keratin.

The compounds of formulae (1)-(3) which can be used in the process of the invention and therefore also the novel compounds of formulae (1a)-(3a) of the invention can be obtained by processes known per se.

Such a process comprises reacting a pyridyloxyaniline one of the formula

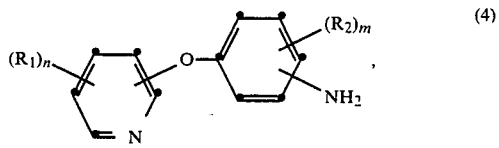
(4)

wherein the general symbols are as defined for formula (1), with trifluoromethanesulfonic anhydride or a trifluoromethanesulfonyl halide in the presence of a base.

Suitable trifluoromethanesulfonyl halides are in particular trifluoromethanesulfonyl chloride and trifluoromethanesulfonyl fluoride. However, the use of trifluoromethanesulfonic anhydride is preferred.

The reaction of a compound of formula (4) with a trifluoromethanesulfonyl halide or with trifluoromethanesulfonic anhydride is conveniently carried out in the presence of a nitrogen base, e.g. a tertiary amine such as pyridine, triethylamine or N,N-dimethylaniline.

The reaction can be carried out in the presence of inert solvents or diluents. Examples of suitable inert solvents or diluents are aliphatic and aromatic hydrocarbons such as cyclohexane, petroleum ether, benzene, toluene and a xylene; halogenated hydrocarbons such as methylene chloride, ethylene chloride, dichloromethane, trichloromethane, chloroform, carbon tetrachloride, tetrachloroethylene and chlorobenzene; ethers and ethereal compounds such as anisole, dioxan, tetrahydrofuran, 1,2-dimethoxyethane and dialkyl ethers such as diethyl ether, diisopropyl ether and tert-butylmethyl ether; nitriles such as acetonitrile and propionitrile; N,N-dialkylated amides such as dimethylformamide and dimethylacetamide; dimethylsulfoxide; ketones such as acetone, diethyl ketone and methyl ethyl ketone; and mixtures of such solvents.

The reaction temperatures are conveniently in the range from $-15°$ C. to $+150°$ C. preferably in the range from $-5°$ to $+120°$ C.

The compounds of formula (1) can be prepared by a further process by reacting a phenolate of the formula

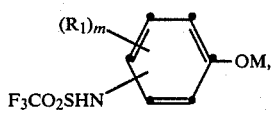 (5)

wherein M is an alkali metal atom or a copper atom and $R_2$ and m are as defined for formula (1), with a compound of the formula

 (6)

wherein X is a halogen atom and $R_1$ and n are as defined for formula (1), in a solvent.

Examples of preferred solvents in this process are pyridine, quinoline, dimethylformamide and the like. It is preferred to use a catalyst, in particular CuCl. The alkali metal salts (M=alkali metal atom) can be used as such or can be formed in situ, e.g. by adding an alkali metal hydroxide or alkali metal alcoholate. The reaction temperature can vary within wide limits depending on the reactivity of the starting materials, as can the reaction times. Generally, the reaction is carried out in the temperature range from 0° to 200° C.

The starting compounds of formulae (4) to (6) to be used in both processes described above as well as the trifluoromethanesulfonyl halides and the trifluoromethanesulfonic anhydride are known or can be prepared by processes known per se. Thus, for example, a compound of formula (4) can be prepared by reacting a compound of the formula

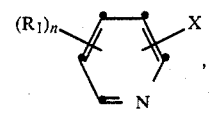 (7)

wherein $R_1$ and n are as defined for formula (1) and X is a halogen atom, preferably fluorine and in particular chlorine, with a compound of the formula

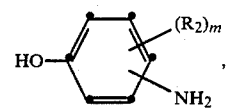 (8)

wherein $R_2$ and m are as defined for formula (1).

The reaction of compounds of formula (7) with compounds of formula (8) is conveniently carried out in the presence of an inorganic or organic base. Examples of inorganic bases are the oxides, hydrides, carbonates and bicarbonates of alkali metals and alkaline earth metals such as sodium hydroxide and sodium hydride; examples of organic bases are in particular tertiary amines such as triethylamine, pyridine and triethylenediamine.

The reaction can be carried out in the presence of an inert solvent or diluent, for example in the presence of one of the media listed above as suitable for the first process for preparing compounds of formula (1). The reaction temperatures are conveniently in the range from 0° to 200° C., preferably in the range from 0° to 150° C.

Compounds of formula (5) can be readily obtained by reacting an aminophenol of formula (8) with a trifluoromethanesulfonyl halide or with trifluoromethanesulfonic anhydride in accordance with the first process of this invention (reaction of the compound of formula (4) with the above-mentioned halides or anhydride) and converting the phenol into a salt.

The starting materials of formulae (7) and (8) are known or can be prepared in a manner analogous to those employed for preparing known compounds.

Alternatively, compounds of formula (4) can be prepared by reducing the corresponding nitro compounds. To this end, conventional reduction methods can be employed, e.g. iron (Bechamp reduction), sodium sulfide and in particular catalytic reduction with $H_2$ (with e.g. Raney nickel as catalyst). The above nitro compounds are known or can be prepared by known processes, e.g. in accordance with the reaction scheme

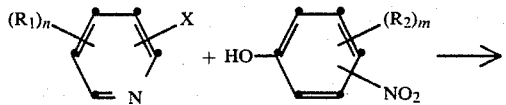

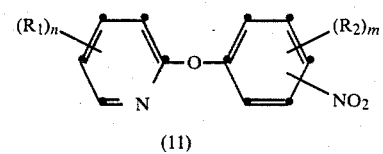

wherein X is chlorine, bromine or iodine and the remaining general symbols are as defined in claim (1).

Although the reaction can be carried out in the presence of a base which acts as catalyst and acid acceptor, it is preferably carried out by a preliminary reaction of a compound of formula (10) with a base to form a salt, with the salts of inorganic bases being preferred. It is known that such salts are readily prepared, namely in situ or isolated. The salts of alkali metals are most preferred, e.g. of sodium and potassium, or the copper salts. If alkali metal salts are used, dimethylformamide and pyridine are the preferred solvents. If $R_2$ is an electron-releasing substituent such as alkyl or alkoxy and is in the 2- or 4-position relative to the nitro group, pyridine is the preferred solvent and a trace of copper(I) chloride is conveniently used as catalyst. For the preparation of 3-phenoxynitrobenzenes it is preferred to use a copper(I) salt or a copper(I) chloride as catalyst and pyridine as solvent. It is advantageous if X is bromine or iodine.

The intermediates described above, where novel, likewise constitute an object of the present invention, as do the processes for the preparation thereof.

The compounds of formulae (1) and (1a) are acid (acid H atom at the substituted amino group). As mentioned previously, they therefore form salts which likewise constitute an object of the invention and can also be used in the process of the invention. These salts are generally metal salts, ammonium salts or organic amine salts (substituted amine salts) and can be prepared by treating the acid form with a stoichiometrically equivalent amount of a suitable base under mild conditions. The metal salts of this invention include alkali metal salts (e.g. lithium, sodium and potassium salts), alkaline earth metal salts (e.g. barium, calcium and magnesium salts) and heavy metal salts (e.g. zinc and iron salts) as well as other metal salts such as aluminium salts. Suitable bases which can be used for the preparation of the metal salts include metal oxides, hydroxides, carbonates, bicarbonates and alkoxides. Some salts are also prepared by cation exchange reactions (by reacting a salt of the invention with an organic or inorganic salt by means of a cation exchange reaction). Organic amine salts include the salts of aliphatic amines (e.g. alkylamines), aromatic and heterocyclic amines as well as such amines with a mixture of these structural types. The amines suitable for the preparation of the salts of the invention can be primary, secondary or tertiary and contain preferably not more than 20 carbon atoms. Such amines include e.g. morpholine, methylcyclohexylamine and the like. These amines and the ammonium salts can be prepared by reacting the acid form with a suitable organic base or with ammonium hydroxide. Suitable salts are generally alkali metal salts, ammonium salts and amine salts.

The salts of the invention are also frequently prepared by reacting the starting compounds in an aqueous solution. This solution can be concentrated by evaporation, thus affording the salt of the compounds, generally in the form of a dry powder.

In some cases it may be simpler to use a non-aqueous solvent such as an alcohol or acetone, etc. The solution so obtained is treated to remove the solvent, e.g. concentrated under reduced pressure. Since many of the salts are water-soluble, they are frequently used in the form of aqueous solutions.

The compounds of formulae (1) and (1a) (e.g. obtained by one of the processes described above) can also be converted into other compounds of formulae (1) and (1a) by suitable reactions known per se.

Thus, for example, compounds of formulae (1) and (1a) can be halogenated (preferably chlorinated) or nitrated in order to introduce substituents $R_1$ and $R_2$. These processes can be carried out by known procedures for the nitration or halogenation (chlorination) of aromatic compounds. The preparation or conversion of salts has already been explained.

The following Examples illustrate in more detail the process of the invention as well as the preparation of compounds of formula (1) and the novel compounds of formula (1a) used therein. It must, however, be emphasised that the invention is not restricted to these Examples.

In the following Examples, as also in the entire description and claims, parts and percentages are by weight unless otherwise stated. Melting points are uncorrected.

EXAMPLE 1

14.8 g of trifluoromethanesulfonic anhydride are added dropwise at $-15°$ C. to 13 g of 4-(5-trifluoromethylpyridin-2-yl-oxy)aniline and 6.1 g of N,N-dimethylaniline in 100 ml of dichloromethane. After the reaction mixture has warmed to room temperature, it is left to stand until the onset of crystallisation. The crystalline solid is then filtered off and taken up in ethyl acetate. The solution is washed twice with 1 N hydrochloric acid and then twice with an aqueous solution of sodium chloride, dried, decolorised with activated carbon and concentrated by evaporation, affording 4-(5-trifluoromethylpyridin-2-yl-oxy)trifluoromethanesulfonanilide of the formula

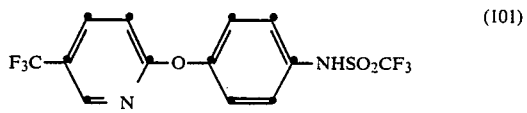

(101)

with a m.p. of 162°–165° C.

The required starting 4-(5-trifluoromethylpyridin-2-yl-oxy)aniline can be prepared as follows:

11.2 g (0.2 mole) of potassium hydroxide in 15 ml of water are added dropwise under nitrogen atmosphere to 22 g (0.2 mole) of 4-aminophenol in 100 ml of diemthylsulfoxide. 36 g (0.2 mole) of 2-chloro-5-(trifluoromethyl)pyridine in 30 ml of dimethylsulfoxide are added dropwise at 25° C. The reaction mixture is stirred for 3 hours at room temperature, then poured into ice-water and extracted with ethyl acetate. The organic phase is dried over sodium sulfate and concentrated by evaporation. The residue is dissolved in ether and the ether solution is extracted with 1 N hydrochloric acid. The acid phase is made alkaline with concentrated NaOH solution and extracted with ether. The ether phase is dried over sodium sulfate and concentrated by evaporation, affording 4-(5-trifluoromethylpyridin-2-yl-oxy)aniline as a brown oil.

EXAMPLE 2

8.5 g of trifluoromethanesulfonic anhydride are added dropwise at $-15°$ C. to 7.6 g of 3-(5-trifluoromethylpyridin-2-yl-oxy)aniline and 3.6 g of N,N-dimethylaniline in 50 ml of dichloromethane. After the reaction mixture has warmed to room temperature, it is diluted with ethyl acetate, washed twice with 1 N hydrochloric acid and then twice with 2 N NaOH solution. The organic phase is dried, clarified and concentrated by evaporation. The crystalline residue is washed with ether, dissolved in ethyl acetate and the solution is shaken with 1 N hydrochloric acid, then dried and concentrated by evaporation, affording 3-(5-trifluoromethylpyridin-2-yl-oxy)trifluoromethanesulfonanilide of the formula

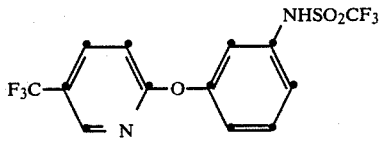 (201)

with a m.p. of 151°–153° C.

EXAMPLE 3

Syridyloxytrifluoromethanesulfonanilides of the formula

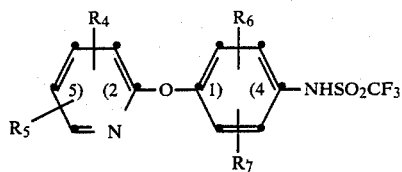 (A)

listed in the following Table can be obtained by a procedure analogous to that described in Examples 1 and 2 by using the corresponding starting materials.

TABLE

| Compound No. | $R_4$ | $R_5$ | $R_6$ | $R_7$ | m.p.(°C.) |
|---|---|---|---|---|---|
| 301 | 5-$CF_3$ | H | 2-$CH_3$ | H | 143–145 |
| 302 | 3-Cl | 5-Cl | 2-$CH_3$ | H | 162–165 |
| 303 | 5-$CF_3$ | H | 3-$CH_3$ | H | 136–137 |
| 304 | 5-$CF_3$ | 3-Cl | H | H | 103–105 |
| 305 | 3-Cl | 5-Cl | H | H | 133–135 |
| 306 | 5-$CF_3$ | 3-Cl | 3-$CH(CH_3)_2$ | H | 175–178 |
| 307 | 5-$CF_3$ | H | 3-$CH(CH_3)_2$ | H | 145–147 |
| 308 | 5-$CF_3$ | 3-Cl | 3-$CH_3$ | 5-$CH_3$ | 160–162 |
| 309 | 5-$CF_3$ | H | 3-$CH_3$ | 5-$CH_3$ | 154–156 |
| 310 | 5-$CF_2CFCl_2$ | 3-Cl | H | H | 134–136 |
| 311 | 5-$CF_3$ | H | 2-Cl | 6-Cl | 165–168 |
| 312 | 5-$CF_3$ | 3-Cl | 2-Cl | 6-Cl | 127–129 |
| 313 | 3-Cl | 5-Cl | 3-$CH_3$ | 5-$CH_3$ | 178–180 |
| 314 | 3-Cl | 5-Cl | 3-$CH(CH_2)_2$ | H | 139–141 |
| 315 | 3-Cl | 5-Cl | 3-$CH_3$ | H | 148–150 |
| 316 | 5-$CF_3$ | 3-Cl | 3-$COOCH_3$ | H | 151 |

The compounds of the following formulae are also obtained in analogous manner:

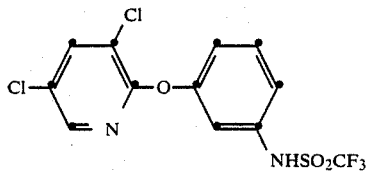 (317)

with a m.p. of 172°–176° C. and

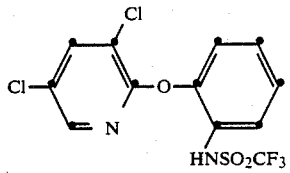 (318)

with a m.p. of 90°–91° C.

EXAMPLE 4

A 0.4% stock solution of the compound of formula (303) in ethylene glycol monomethyl ether is prepared. Then an aqueous treatment bath containing, in 120 ml of distilled water, 0.12 ml of a wetting agent and dispersant, 0.6 ml of formic acid 1:10 and 0.75 ml of the 0.4% stock solution, is prepared at room temperature. Then 3 g of wool flannel are wetted with hot water and put into the bath at room temperature. While constantly cirulating the wool sample, the bath temperature is raised to 98° C. in the course of 20 minutes and treatment is carried out for 60 minutes at 98° C. The bath is then cooled, the wool sample rinsed twice for 3 minutes with distilled water, squeezed out by hand and dried in the air. The active ingredient concentration is 1000 ppm, based on the weight of the wool.

The dried sample is subjected to the mothproofing test (protection against feeding damage caused by the webbing clothes moth *Tineola biselliella Hum.*) and to the resistance test against larvae of the fur beetle (*Attagenus piceus Oliv*) and carpet beetle (*Anthrenus flavipes*) in accordance with SNV 195901. In these tests, 4-week-old larvae of *Tineola biselliella* or *Anthrenus flavipes* and 6- to 7-week-old larvae of *Attagenus piceus* are used. Pieces of the same size are cut out of the treated wool samples and subjected for 14 days at constant temperature (28° C.) and constant relative humidity (65%) to attack (feeding) by 15 larvae of each of the pests. Evaluation is made on the one hand according to the relative loss in weight of the test sample and, on the other, according to the number of still living organisms.

The tested compound exhibits an excellent action against all three pests.

Wool samples with an excellent protective finish against the three tested pests are also obtained by substituting one of the compounds of formula (101, (201), (301), (304), (306)–(309) and (313)–(315) for the compound of formula (303) and repeating the above procedure.

EXAMPLE 5

A 0.4% stock solution of the compound of formula (303) in ethlyene glycol monomthyl ether is prepared. The stock solution (12.5 ml) is diluted to 50 ml (solution 1) with ethylene glycol monomethyl ether which contains 0.65 g/l of a wetting agent and dispersant. Solution 1 (25 ml) is then diluted to 50 ml (solution 2) with ethylene glycol monomethyl ether which contains 0.65 g/l of a wetting agent and dispersant. Solution 2 (25 ml) is diluted in turn to 50 ml (solution 3) with ethlyene glycol monomethyl ether which contains 0.5 g/l of a wetting agent and dispersant.

3 ml of each of solutions 1, 2 and 3 are poured into crystallisation dishes and a disc of wool flannel is wetted for 3 seconds therein. The moist discs are then padded between aluminium sheets to a pick-up of 50% of each solution. The concentrations of active ingredient are, respectively, 500 ppm, 250 ppm and 125 ppm for the discs treated with solutions 1, 2 and 3. The discs are then dried in the air and subjected to the same biological tests as in Example 4.

The tested compound exhibits an excellent action against all three pests.

Wool samples with an excellent protective finish against the three tested pests are also obtained by substituting one of the compounds of formulae (101), (201), (301), (304), (306)–(309) and (313)–(316) for the compound of formula (303) and repeating the above procedure.

EXAMPLE 6

A 10% solution of the compound of formula (315) in ehtlyene glycol monomethyl ether is prepared. One part by volume of this solution is diluted with 200 parts by volume of a solvent suitable for dry cleaning, for example a suitable petroleum fraction or perchloroethylene. If desired, cleaning promoters can be added. Woollen articles are then treated in the conventional manner in this cleaning fluid and subsequently centrifuged to a solvent pick-up of about 100% of the weight of the wool. After drying, the articles have an excellent protective finish against the above-named pests that feed on keratin.

BEISPIEL 7

A 0.5% solution of the compound of formula (315) in methylene chloride, trichloroethylene or a low boiling petroleum fraction is prepared. A woollen article is sprayed with this solution from a conventional spray device, so that $2 \times 15$ g/m² of active ingredient solution is applied, corresponding to a concentration of about 400 ppm of the compound of formula (315) on the material at a 30% consumption of the aerosol. The treated woollen fabric is protected against the above-named pests that feed on keratin.

Wool samples with a protective finish against the above-named pests that feed on keratin can also be obtained by substituting in Examples 6 and 7 one of the compounds of formulae (201), (301), (303), (304), (306)–(309), (313) and (314) for the compound of formula (315) and repeating the procedure as described therein.

EXAMPLE 8

Dyeing and simultaneous mothproof and beetle-resistant finish: In a dyeing apparatus, a piece of wool fabric is prewetted for 5 minutes at 40° C. in 600 g of a dye liquor comprising 0.15 g of the compound of formula (303),
30.3 g of Glauber's salt,
24.0 g of conc. sulfuric acid,
3.0 g of a red dye of the formula

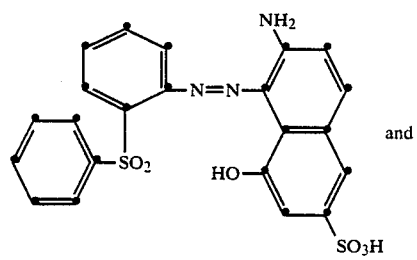

and 541.5 g of demineralised water.

The liquor to goods ratio is 1:20.

The liquor is then heated over 45 minutes to about 98° C. After it has been treated for 1 hour at this temperature, the wool fabric is rinsed and dried. The dye as well as the compound of formula (303) have exhausted onto the fabric. After this single bath treatment, the red woollen fabric is fully protected against feeding damage by the larvae of moths and beetles. This is confirmed by the resistance test according to SNV Standards 196901 and 195902.

EXAMPLE 9

Application by aftertreatment bath: In a dyeing apparatus, a piece of wool fabric is prewetted for 5 minutes at 30° C. in 400 g of an aftertreatment bath comprising
0.1 g of the compound of formula (303)
4 g of 85% formic acid and
395 g of demineralised water.

The liquor to goods ratio is 1:20.

The bath is then warmed over 20 minutes to 45° C. and after it has been treated at this temperature for 30 minutes with constant agitation, the wool fabric is thoroughly rinsed in cold water and dried. The treated fabric is fully protected against the larvae of wool pests.

Fabrics with a good protective finish against wool pests can also be obtained by substituting in Examples 8 and 9 one of the compounds of formulae (101), (201), (301), (304), (306)–(309) and (313) to (316) for the compound of formula (303).

What is claimed is:

1. A process for providing keratinous material with a protective finish against attack by insects that feed on keratin, which process comprises treating the material to be protected with a compound of the formula

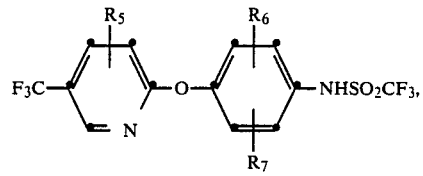

wherein
R₅ is hydrogen or chlorine,
R₆ is hydrogen, methyl or isopropyl and
R₇ is hydrogen or methyl.

2. A process of claim 1 wherein one or both of R₆ and R₇ are ortho to the —NHSO₂CF₃ group and at least one of R₆ and R₇ is not hydrogen.

3. The process of claim 1 wherein R₅, R₆ and R₇ are all hydrogen.

4. A process according to claim 1, which process comprises treating the material to be protected with an aqueous liquor containing one or more of the compounds defined in claim 1.

5. A process according to claim 1, which comprises treating the material to be protected with an organic cleaning liquid containing one or more of the compounds defined in claim 1.

6. A process according to claim 1, which comprises spraying the material to be protected with an organic solvent containing one or more of the compounds defined in claim 1.

7. A process according to any one of claims 4 to 6, which comprises applying to the material to be protected the active compounds in an amount of 10 to 2000 ppm, based on said material.

8. A process according to claim 4, which comprises treating woolen textiles in a dye bath by the exhaust process.

9. A process according to claim 4, which comprises treating woolen textiles in an aftertreatment bath by the exhaust process.

10. The keratinous material finished according to claim 1.

11. The keratinous material according to claim 10 which contains 10 to 2000 ppm of a compound of the formula.

* * * * *